US006527996B2

(12) United States Patent
Schiraldi et al.

(10) Patent No.: US 6,527,996 B2
(45) Date of Patent: Mar. 4, 2003

(54) PROCESS OF MAKING A TUBULAR DENTAL HYGIENE DEVICE

(75) Inventors: Michael Thomas Schiraldi, East Brunswick, NJ (US); John Charles Subelka, Marlboro, NJ (US); Ralph Korpman, Bridgewater, NJ (US); Bruce C. Johnson, Whiting, NJ (US); Atiye Erden Tanverdi, Columbia, SC (US); Ivor Peter Lewis, Columbia, SC (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 25 days.

(21) Appl. No.: 09/774,460

(22) Filed: Jan. 31, 2001

(65) Prior Publication Data

US 2001/0003587 A1 Jun. 14, 2001

Related U.S. Application Data

(62) Division of application No. 09/290,637, filed on Apr. 12, 1999, now Pat. No. 6,251,410, which is a continuation of application No. 08/923,157, filed on Sep. 4, 1997, now abandoned, which is a continuation of application No. 08/614,233, filed on Mar. 12, 1996, now abandoned, which is a continuation of application No. 08/254,216, filed on Jun. 6, 1994, now abandoned.

(51) Int. Cl.$^7$ .......................... D01D 5/098; D01D 5/24; D01D 5/253; D01D 10/02

(52) U.S. Cl. ................ 264/167; 264/178 F; 264/209.1; 264/209.3; 264/210.2; 264/210.8; 264/211.12; 264/211.17; 264/235.6

(58) Field of Search ......................... 264/167, 178 F, 264/209.1, 209.3, 210.2, 210.8, 211.12, 211.17, 235.6

(56) References Cited

U.S. PATENT DOCUMENTS

| 4,386,187 A | * | 5/1983 | Grancio et al. |
| 4,386,188 A | * | 5/1983 | Grancio et al. |
| 4,767,817 A | * | 8/1988 | Lee |
| 5,098,711 A | * | 3/1992 | Hill et al. |
| 5,392,795 A | * | 2/1995 | Gathani |
| 5,503,842 A | * | 4/1996 | Fazan et al. |
| 6,016,816 A | * | 1/2000 | Ariagno |

FOREIGN PATENT DOCUMENTS

| JP | 05184605 A | * | 7/1993 |
| WO | WO-9534252 A1 | * | 12/1995 |

* cited by examiner

Primary Examiner—Leo B. Tentoni

(57) ABSTRACT

This invention relates to a novel composition for use in dental flosses or tapes. More particularly, it relates to novel compositions containing a base polymer, a block copolymer and a nonmigrating compatibilizer or plasticizer that, in combination in a blend, result in a floss or dental tape having good breaking strength, elongation, tenacity, nick resistance and gentleness to the gums.

4 Claims, 1 Drawing Sheet

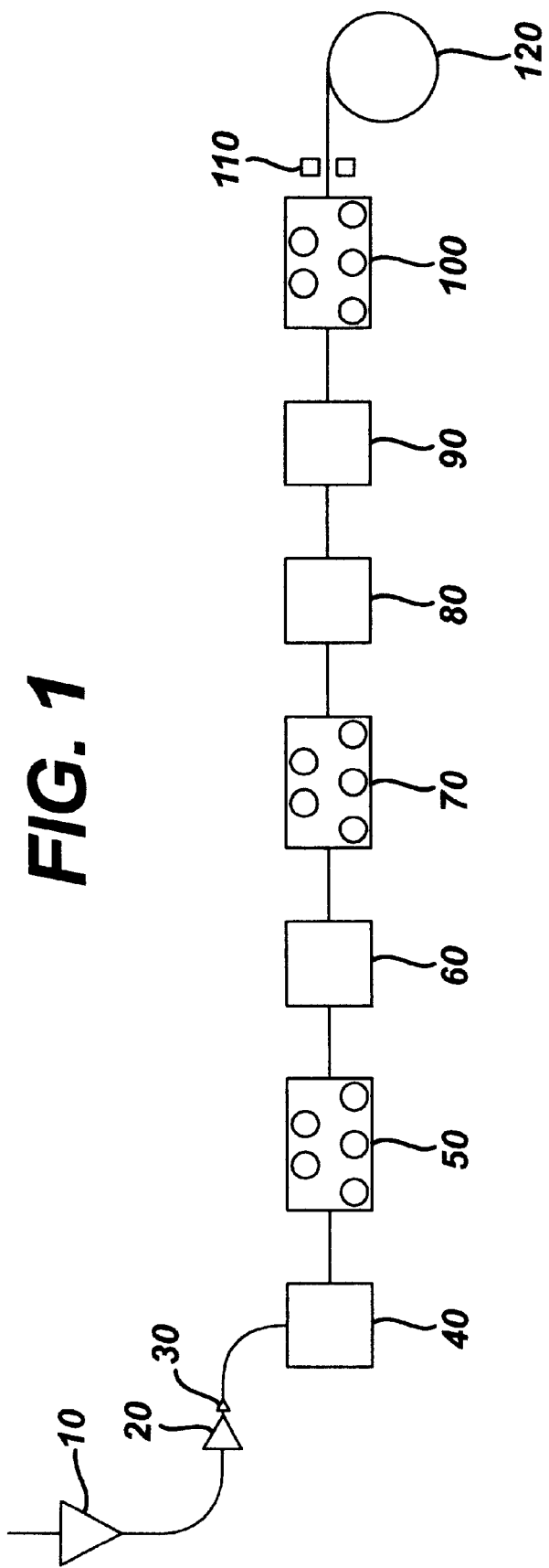

PROCESS OF MAKING A TUBULAR DENTAL HYGIENE DEVICE

CROSS REFERENCE TO RELATED APPLICATIONS

This is a divisional of application Ser. No. 09/290,637, filed Apr. 12, 1999, now issued as U.S. Pat. No. 6,251,410, which is a continuation of application Ser. No. 08/923,157, filed Sep. 4, 1997, now abandoned, which is a continuation of application Ser. No. 08/614,233, filed Mar. 12, 1996, now abandoned, which is a continuation of application Ser. No. 08/254,216, filed Jun. 6, 1994, now abandoned.

BACKGROUND OF THE INVENTION

1. Field of the Invention

This invention relates to a novel composition for use in dental flosses or tapes. More particularly, it relates to novel compositions containing a base polymer, a block copolymer and a nonmigrating compatibilizer or plasticizer that, in combination in a blend, result in a floss or dental tape having good breaking strength, tenacity, nick resistance and elongation properties. It also relates to a novel extruded, flattened, monofilament tube structure useful in dental tapes and flosses, as well as a method for making such structure. It also relates to a flattened monofilanent tube that is textured along the longitudinal axis as well as perpendicular to this axis.

2. Prior Art

The use of polymer compositions in dental flosses and tapes has been known previously. However, there have been continuous efforts to develop a floss which does not shred or fray upon use and which has sufficient tensile strength for use between the teeth.

For example, U.S. Pat. No. 2,381,142 (Stonehill) describes a dental floss made from a strand or filament of synthetic fibers of an unplasticized vinyl resin such as a copolymer of vinyl chloride and vinyl acetate treated with wax.

U.S. Pat. No. 3,359,344 (Fukushima) describes a method for manufacturing a spun fiber. According to Fukushima, a polymer selected from the group of polyethylene, polypropylene and polystyrene having a melting point lower than 170° C. is mixed with a second polymer selected from polyamides and polyesters having a melting point greater than 170° C. and an additional amount of the first polymer. The composition is blended and extruded to form a fiber.

In U.S. Pat. No. 3,639,505 (Hughes et al.), there is described a method of improving the dyeability of polyolefin fibers and films. The method includes forming a polymer alloy containing a blend of polyolefin, a minor amount of polyethylene terephthalate and from 0.2 to 5 parts per hundred parts of polymer of toluenesulfonamide compound.

U.S. Pat. No. 3,800,812 (Jaffe) describes a dental floss made from a polyester elastomer, including Hytrel (available from DuPont). The elastomer is extruded into a hot and tacky tape, then cooled.

U.S. Pat. No. 3,900,549 (Yamane et al.) describes a method for preparing composite filaments composed of a polyethylene and a polyester. The method includes the steps of mixing a polyethylene having a melt index of above 27 with a polyester having a specific inherent viscosity, the proportion of the polyethylene being 5 to 15% or 25 to 90% based on the total weight of the mixture, melt extruding the resulting mixture through a spinneret and then withdrawing the extruded filaments at a speed of above 2,500 meters per minute.

U.S. Pat. No. 3,957,056 (Ferraro et al.) describes a dental floss containing aromatic polyamide fibers having at least 35% of the amide linkages attached directly to two aromatic rings.

U.S. Pat. No. 4,552,603 (Harris, Jr. et al) describes heat bondable bicomponent fibers containing polyester and another thermoplastic polymer having a melting point which is at least 15% C. below that of polyester.

U.S. Pat. No. 4,583,564 (Finkelstein et al.) describes a dental floss consisting of filaments containing a higher melting point core material and a lower melting point sheath material. The sheath material fibers are fused by subjecting them to a temperature sufficient to fuse them.

U.S. Pat. No. 4,609,710 (Iohara et al.) describes an undrawn polyester yarn and process for manufacturing such yarn. The main acid component of the yarn is an aromatic dicarboxylic acid.

U.S. Pat. No. 4,986,288 (Kent et al.) describes dental floss and toothpicks which contain one or more coagulants to retard and stop bleeding during flossing.

U.S. Pat. No. 4,996,056 (Blass) describes a dental floss or tape containing fluorocarbon polymer powder particles as a solid lubricant.

Despite the existence of such products as described heretofore, there still exists a need for dental floss and tape products having high breaking strength, high tenacity, nick resistance and suppleness which does not fray or break easily when used. Furthermore, there is a need to have dental floss or tape which is gentle to gum tissue which can be manufactured at high speed and low cost.

It is, therefore, an object of this invention to provide an extruded, flattened, monofilament tube with rounded edges suitable for use as a dental floss or tape.

It is another object of this invention to provide a flattened, monofilament tube that is textured along the longitudinal axis as well as perpendicular to this axis.

It is another object of this invention to provide a polymer blend resulting in an acceptable dental floss or tape.

It is another object of this invention to provide a dental floss or tape having high breaking strength, high tenacity, nick resistance and suppleness which does not fray or break in use.

Another object of this invention is to provide a method for making a polymer blend resulting in an excellent composition for use in dental flosses and tapes.

Another object of this invention is to provide a method of making polymer blend products in the form of a monofilament for use as a dental tape or floss.

Yet another object of this invention is to provide low cost, high grade polymer compositions for use in dental flosses and tapes.

Additional objects will become apparent throughout the ensuing description of the products and processes of this invention.

SUMMARY OF THE INVENTION

This invention relates to novel compositions useful in making dental flosses and tapes. The compositions of this invention are extrudable and can be formed into a monofilament.

Dental flosses and tapes made with the novel compositions of this invention may be formed into an extruded, flattened, monofilament tube with rounded edges. The unique monofilament shape provides rounded edges that will not cut or irritate gingiva tissue. The composition allows the monofilament to meet two primary concerns of the dental floss consumer: ease of passage between teeth and resistance to fraying. The composition provides a supple, slippery material that is capable of sliding and compressing as it moves between teeth. The individual fiber composing the novel monofilament structure and composition does not break and is not perceived to fray as do ordinary dental flosses, which are composed of many fine monofilaments. It has been found that, upon preparation for use, the user generally stretches the floss or tape prior to insertion between the teeth. We have discovered that the flosses of this invention elongates and reduces its thickness such that it easily slides between the teeth. The monofilaments of this invention can elongate at least about 30% of their original length and can reduce their thicknesses at least about 10%.

The flosses of this invention can be textured along the longitudinal axis as well as perpendicular to this axis. This textured floss, which still slides easily between the teeth due to its unique composition, enhances the floss' effectiveness by exerting gentle pressure interstitially.

More particularly, the products of this invention relate to novel compositions containing a base polymer, such as a polyolefins, modified polyamides, polyesters or polyurethanes; block, or segmented, copolymers such as modified polyamides, polyesters or polyurethanes; and nonmigrating compatibilizer(s) or plasticizer(s) that in combination result in a polymer blend which can be formed into a monofilament having good breaking strength, tenacity, nick resistance and elongation properties.

The products of this invention are considered, generally, "polymer blends". Polymer blend technology involves the mixture of different polymers, and has been necessitated by the increasing costs of synthesizing new polymer structures. It has been discovered that certain polymer blends, surprisingly, exhibit novel, unusual and unexpected properties different from the constituent polymers. The blending of polymers with careful control of the resulting blend's morphology by consideration of the rheological and thermodynamic properties of the individual components have led to new polymer blends of commercial interest.

The compositions of this invention generally have three constituent components: a base polymer, a block copolymer and a compatibilizer. The base polymer, which is selected from the group of polyolefins, modified polyamides, polyesters or polyurethanes, provides strength and tenacity; it may also impart suppleness. The segmented or block copolymer component assists in providing nick resistance and elasticity. In general, many polymer pairs are thermodynamically incompatible. In order to facilitate intimate polymer blending, a polymeric compatibilizer should be introduced into the compositions of this invention. The compatibilizer acts as a molecular bridge between the polymers, similar to the action of a surfactant in emulsifying oil and water systems. Thus, the nonmigrating compatibilizer assists in providing integrity to the composition. This, in turn, contributes to the suppleness of the compositions and assists in melt processing and post-extrusion drawing of the monofilament tube by reducing melt viscosity and improving elongation characteristics.

The compositions of this invention are used in making flosses and tapes having excellent attributes. In use, dental flosses and tapes must have a high breaking strength, high tenacity and a suitable denier and thickness. They should also have a softness or suppleness such that they can easily be handled by the consumer. In practice, the dental floss or tape must not easily nick and break when the consumer encounters a sharp edge in flossing teeth and must not elongate too readily. The polymer blends of this invention have all of these attributes. In addition, they are capable of being pigmented, readily processible on extruders using tubular die or spinneret die technology and may be waxed to accept flavors.

The products of this invention may be made by blending all the individual polymers in pellet or powder form in a dry mixer. They are then compounded on a twin screw compounding extruder and pelletized. Additionally, the individual polymer pellets may be gravity fed to a twin screw compounder to form the pellets of the compounded polymer blend. The compounded pellets are then extruded in a single screw extruder with a die head having an appropriate tubular or spinneret die. The extruded polymer is drawn down in a highly oriented form, annealed and calendered to achieve an appropriate thickness.

BRIEF DESCRIPTION OF THE DRAWINGS

The invention will be more clearly understood with reference to the accompanying Drawing wherein FIG 1. illustrates an apparatus and method of making dental flosses and dental tapes.

DETAILED DESCRIPTION OF THE PREFERRED EMBODIMENTS

Preferably, the base polymer is a high molecular-weight polymer having high tensile strength, suppleness and tenacity. The base polymer should be capable of contributing these properties to the final product such that the resulting dental tape or floss has a tenacity (defined as strength per unit weight) of between about 2 about 6 g/denier and, more preferably between about 2.5 and about 3.7 g/denier. Most preferably, the tenacity of the final product should be between about 2.8 and about 3.2 g/denier.

The base polymer of the compositions of this invention may include polyolefins, modified polyamides, polyesters or polyurethanes. Polyolefins having suitable strength for use in the products of this invention are, for example, polypropylene, Valtec HH-442H (available commercially from Himont U.S.A. Inc., of Wilmington, Del.); modified polyolefins Profax KT-012P (or its equivalent, Himont Profax KT-025P) and Profax KS-031P (available commercially from Himont U.S.A. Inc. of Wilmington, Del.); Extrall 202.01 (available commercially from Exxon Corp). One or more polymers may be used in the base polymer constituent portion of the products of this invention.

The modified polyolefins useful in the products of this invention are preferably modified polypropylenes. Preferably, they impart two advantageous properties to the compositions of this invention: tenacity of the resultant floss and suppleness. Together, these properties contribute to the "stretchability" of the floss.

Modified polyamides having suitable strength for use in the products of this invention are, for example, Pebax X1147 (available commercially from Atochem North America of Philadelphia, Pa.).

Modified polyesters having strength suitable for use in the products of this invention are, for example, Hytrel G4778 (available commercially from Dupont Company of Wilmington, Del.). Modified polyurethanes having strength suitable for use in the products of this invention are, for example, Estane 58091 (available commercially from B.F. Goodrich Company of Brecksville, Ohio).

The block copolymer constituent of the compositions of this invention contribute to the tear strength and "nick" resistance of the floss compositions of this invention. Thus, the compositions of this invention will not tear when subjected to a small cut or nick. Rather than permitting the tear to propagate along the product, the compositions of this invention impede the propagation of nicks. Preferably, the block copolymer useful in the compositions of this invention are composed of a "hard" segment and a "soft" segment. The "hard" segments contribute to the strength of the polymer, while the "soft" segments increase its suppleness. The hard segments tend, generally, to be more compatible with each other than with the soft segments. In the composition, they tend to be attracted to each other and form clusters. These clusters tend to impede the propagation of nicks or cuts by standing in the path of a cut.

Preferably, the segmented or block copolymer is a modified polyamide, polyester or polyurethane. Modified polyamides that contribute significantly to nick or cut resistance are, for example, Pebax 5533 (available commercially from Atochem North America of Philadelphia, Pa.). Modified polyesters that contribute significantly to nick or cut resistance are, for example, Hytrel 4056 (available commercially from Dupont Company of Wilmington, Del.). Modified polyurethanes that contribute significantly to nick or cut resistance are, for example, Estane 58137 (available commercially from B.F. Goodrich of Brecksville, Ohio).

The compatibilizer portion of the compositions of this invention assist in maintaining the integrity of the compositions. They interact with both the base polymer and the block copolymer in order to "glue" them together in the blend. This activity contributes to reducing the melt viscosity, which in turn improves processing and aids in elongation, thus maintaining the blend's suppleness at room temperature.

Preferably, the compatibilizer or plasticizer component is a nonmigrating polymer. Of course, those of ordinary skill in the art will be aware that the appropriate compatibilizer for each composition according to this invention will be different, depending upon the polymers which constitute the remainder of the composition. So long as the compatibilizer contains substituent groups which are compatible with both the base polymer and the block copolymer, the compatibilizer will be an appropriate choice for use in the compositions of this invention. Nonmigrating plasticizers that contribute significantly to suppleness, reduce melt viscosity and improve drawing characteristics of the extruded monofilament are, for example, Elvaloy HP441 (available commercially from Dupont Company of Wilmington, Del.), a terpolymer of ethylene, carbon monoxide and butyl acrylate; Polybond 1002 (available commercially from BP Chemicals of Hackettstown, N.J.), a propylene polymer having acrylic acid end groups; or Orevac 9314 (available commercially from Atochem North America of Philadelphia, Pa.), a propylene copolymer also having acrylic acid end groups.

The preferred compatibilizer for a composition containing a polyolefin base polymer and a polyester block copolymer is a terpolymer of n-butylacrylate, carbon monoxide and ethylene. This polymer has a very high molecular weight (about 400,000), with a low melting point (about 65° C). The amount of n-butyl acrylate present as a free monomer is about 10% maximum. The boiling point of n-butyl acrylate is about 145–6° C. During processing, when temperatures of 220° C. are seen, any remaining free monomer is volatilized and removed from the melt. The thermal stability measured on the floss ribbon also indicates that the polymers are stable up to about 275–300° C.

Preferably, the compositions of this invention contain as their base polymer one or more polyolefins. The preferable block copolymer is a modified polyester. Preferably, the compatibilizer is n-butyl acrylate, ethylene, carbon monoxide terpolymer. Most preferably, the composition of this invention should contain Himont Profax KT-012P polyolefin (or its equivalent, Himont Profax KT-025P), Himont Profax KS-031P polyolefin, DuPont Hytrel 4056 polyester block copolymer and DuPont Elvaloy HP 441 n-butyl acrylate, ethylene carbon monoxide terpolymer.

Of course, the ranges of concentrations of the base polymer, block copolymer and compatibilizer will vary depending upon the constituent polymers. For example, a preferred range of base polymer when the base polymer is polyolefin is between about 30 and about 50 weight percent of the composition. In such a polyolefin-based composition, a preferred range of polyester block copolymer is between about 30 and 50 weight percent of the composition. The preferred range of compatibilizer is between about 2.5 and about 7.5 weight percent of the composition. In other systems, such as a polyamide system, the preferred ranges are as follows:between about 5 and about 15 weight percent of the base polymers, between about 10 and about 70 weight percent of the block polyamide, and between about 3 and about 15 weight percent of the compatibilizer.

Most polymer blends are intimate mixtures of the individual polymers. The term "intimate" refers to the domain or size of the individual polymers. If improperly processed, the domain size may be on the order of tens to hundreds of microns, and may be visible to low power light magnification. Such a polymer blend tends to have inferior properties. The more intimate the mixture, the better its physical properties. The polymer blends of this invention are preferably made using techniques which result in homogeneous materials on a micro-scale. Preferably, the blends of this invention are compounded using a twin-screw compounding extruder. The use of a twin-screw extruder results in high shear mixing in localized areas. Preferably, a Werner Pfleiderer ZSK 30 or ZSK 58 twin-screw compounding extruder may be used, or an American Leistritz 40 or 34 may be used. Other twin-screw compounding extruders known to those of ordinary skill in the art may also be used to compound the compositions of this invention. Other acceptable methods of compounding the compositions of this invention include batch mixers using Banbury Mills, Brabender Plasticorders or the like.

Preferably, the flattened, tubular dental floss is produced by extruding a unique polymer blend into a small and thin tubing and subsequently oriented (or "drawn"), annealed, collapsed ("flattened") and wound on a spool. A double walled product, with high tensile strength and tear, or "nick" resistance is formed. The round edges of the flattened tube eliminate the cause for gum irritation.

The initial diameter and wall thickness of the "as-extruded" tube are functions of the inside and outside diameter of the female and male tubing die components.

An appropriate tubular die useful in extruding flosses has the dimensions of about 0.212 inches (outer diameter) for the male portion and about 0.222 inches (inner diameter) for the female portion. Other dimensions may be used, in accordance with the teachings in the art, however, the aforementioned dimensions are preferred. When a spinneret die is used, hollow filaments are extruded by the suitable arrangement and design of orifices such that the polymer melt fuses below the spinneret before entering the water quenching bath. Preferably, a "C"-shaped spinneret die is used, through which the polymer melt is extruded. As the polymer melt flows through the spinneret die and proceeds toward the cooling bath, the polymer located on the ends of the "C" fuse together and form a hollow tube. The preferable dimensions for the "C"-shaped spinneret die are about 0.1000 inches (outer diameter) and about 0.0896 inches (inner diameter), with an allowance of about 0.0200 inches between the "ends" of the "C". Of course, other dimensions may be utilized in accordance with the teachings in the art. In both methods of forming the hollow tube or filament, gas or air can be injected into the tube in the melt stage to help control the wall thickness.

The polymer blend is extruded through a series of zones, each subjecting the extruded material to a progressively higher temperature through four temperature zones. For example, the first zone has a temperature of about 350° F., the second zone, about 420° F., the third, about 440° F., at which point the blend material melts and the fourth, about 470° F., at the die head. The extruded tube is then quenched in a quench bath at a temperature of about 75 to about 80° F. The resulting fiber is pulled through a series of five Godet rolls at about 20 rpms. The fiber is then pulled through a water bath at about 205° F. during stretching. Heating the fiber quickly during stretching reduces the formation of fibrils. The fiber is then stretched in the hot water bath over a length of six feet to a second series of Godet rolls at about 145 rpms. The fiber is then annealed by pulling it through an annealing oven at 205° F. to stabilize the structure and prevent shrinking. The maximum draw ratio of the process is about 7.25:1. The annealing process is performed through a third series of Godet rolls at a speed of about 140 rpms with the overall draw ratio being about 7:1. Other draw ratios may be used, depending on the polymer blend composition. Other ratios used were: 7.0:1.0 maximum and 6.5:1.0 overall; 6.75:1.00 maximum and 6.25:1.00 overall. The filament is then calendered, flattened and wound up onto spools for subsequent waxing and made into bobbins for consumer use.

Preferably, the dimensions of the flattened, tubular monofilament are between about 2 and about 4.5 mils in thickness and, the width between about 0.025 to about 0.070 inches when the denier is in the range of about 700 to about 900. Most preferably, the monofilament is about 2.5 mils to about 3 mils in thickness at this denier. When higher deniers are used, e.g., from about 1200 to about 1300, the preferred thickness is between about 2 mils and about 4.5 mils, but the width should preferably be between about 50 mils and about 80 mils. When the denier range is in the range of between about 600 and about 900, the preferred thickness should be between about 2 mils and about 4.5 mils and the width should be between about 25 and about 35 mils. This enables us to make ribbons or tapes with a broad range of widths suitable for use in dental hygiene.

Referring to FIG. 1, there is illustrated a method of making flosses and dental tapes of this invention. Polymer blend pellets are fed into a dryer/feed hopper, 10, through which the resin travels to an extruder, 20. The polymer is extruded through a die head, 30, forming a monofilament, and is then deposited into a water quench bath, 40. Water quench bath 40 should be kept at a temperature relatively lower than the temperature of the polymer resin as it exits the extruder 20. For example, water quench bath 40 may be kept at about 70° F. After travelling through water quench bath 40, the monofilament is drawn through Godet A, 50, which causes the monofilament to elongate. Godet A, 50, should run at a speed of about between 10 and 50 revolutions per minute (RPM). More preferably, Godet A should run at a speed of between about 20 RPMS. The monofilament is then drawn through a hot water bath, 60. Hot water bath 60 should be kept at about 150 to about 210° F. Most preferably, it should be kept at about 205° F. After passing through hot water bath 60, the monofilament is drawn through another set of Godet rolls, Godet B, 70, for further extension. Godet B, 70, should run at a speed of between about 130 and about 200 RPM. The speed differential between Godet A, 50, and Godet B, 70, and passing the monofilament through hot water bath 60 assists in elongating the monofilament without breaking it or causing nicks or tears in the filament. From Godet B, 70, the monofilament is routed through annealing oven 1, 80, which is held at about 250° F. and then through annealing oven 2, 90, which is held at about 205° F. This portion of the process assists in stabilizing the compositions of the invention, strengthening the monofilament. The monofilament is then routed through Godet C, 100, which is run at between about 125 and about 140 RPM. Preferably, the monofilament is flattened through calender 110 and then wound around a spool at rewind station 120.

The following examples serve to illustrate the compositions and methods of this invention, however, it should be understand that the compositions and methods of this invention are not limited to the illustrated embodiments.

EXAMPLE 1

2550 grams of Extrall 202.01 from Exxon Corporation, a thermoplastic polyolefin believed to be polypropylene modified in a reactor process with a thermoplastic rubber, 300 grams of Hytrel 4056 available from the E.I. dupont de Nemours Corporation of Wilmington, Del., a block copolymer consisting of polybutylene terephthalate and polyether glycols, and 150 grams of Elvaloy HP441 from the Dupont Corporation, a terpolymer made from ethylene, butylacrylate and carbon monoxide monomers, were tumble-blended in a vee blender. The composition was compounded and pelletized on a Werner Pfleiderer ZSK-30 twin screw compounding extruder and subsequently extruded into a monofilament in a Killion (¼ inch) single screw extruder with a tubular die head. The extruded polymer was drawn down, annealed and calendered. The resulting polymer monofilament had reasonable physical properties. Denier, thickness, width, maximum force to break and maximum elongation and tenacity are shown in Table 1. Denier was determined by measuring a length of floss and multiplying to assess the weight of the floss per 9000 meters of filament. Thickness was determined by using a micrometer. Width was measured using a shadowgraph. Breaking strength and percent elongation were determined using the procedures set forth in ASTM D2256, with the samples tested under TAPPI conditions (i.e. 73° F. and 60% relative humidity). Examples 2–6 and 8–35 were similarly tested. The results are set forth in Table I.

EXAMPLES 2 AND 3

Polymers were blended, pelletized, extruded and drawn down as described in Example 1. The components and respective percentages are shown in Table 2.

TABLE 2

|  | Example 2 | Example 3 |
|---|---|---|
| Extrall 202.01 | 80 | 80 |
| Hytrel 4056 | 10 | 15 |
| Elvaloy HP441 | 10 | 5 |

EXAMPLES 4, 5 AND 6

To test the significance of the amount of block copolymer (Hytrel 4056) had on nick resistance, polymers having varying amounts of block copolymer were blended, pelletized, extruded and drawn (as in Example 1); the compositions are shown in Table 3.

TABLE 3

|  | Example 4 | Example 5 | Example 6 |
|---|---|---|---|
| Extrall 202.01 | 75 | 55 | 35 |
| Hytrel 4056 | 20 | 40 | 60 |
| Elvaloy HP441 | 5 | 5 | 5 |

EXAMPLES 7 AND 8

Monofilaments were made in accordance with the procedure described in Example 1. The compositions of Examples 7 and 8 contained Ampacet 11343 from the Ampacet Company, a white pigmented (TiO2) polypropylene concentrate, and are shown in table 4.

TABLE 4

|  | Example 7 | Example 8 |
|---|---|---|
| Extrall 202.01 | 72.5 | 70.0 |
| Hytrel 4056 | 20.0 | 20.0 |
| Elvaloy HP441 | 2.5 | 5.0 |
| Ampacet 11343 | 5.0 | 5.0 |

EXAMPLES 9 AND 10

Monofilaments were made as described in Example 1. The compositions, which contain Polybond 1002 from BP Chemicals Company, a plasticizer a polypropylene grafted with acrylic acid, are set forth in Table 5.

TABLE 5

|  | Example 9 | Example 10 |
|---|---|---|
| Extrall 202.01 | 72.5 | 70.0 |
| Hytrel 4056 | 20.0 | 20.0 |
| Polybond 1002 | 2.5 | 5.0 |
| Ampacet 11343 | 5.0 | 5.0 |

EXAMPLES 11 AND 12

Monofilaments were made as described in Example 1 having the compositions, which contain Hytrel G4778, a block copolymer consisting of polybutylene phthalate and polyetherglycols, are shown in Table 6.

TABLE 6

|  | Example 11 | Example 12 |
|---|---|---|
| Extrall 202.01 | 72.5 | 70.0 |
| Hytrel G4778 | 20.0 | 20.0 |
| Elvaloy HP441 | 2.5 | 5.0 |
| Ampacet 11343 | 5.0 | 5.0 |

EXAMPLES 13, 14 AND 15

Modified polyolefin base polymers were evaluated. These polymers, Himont KS-021P, KS-031P, KS-052P and KS-063P are ethylene propylene polymers. KT-012P is a terpolymer which also contains ethylene and propylene. The compositions are shown in Tables 7–12.

TABLE 7

|  | Example 13 | Example 14 | Example 15 |
|---|---|---|---|
| Himont KS-021P | 70 | — | — |
| Himont KS-031P | — | 70 | — |
| Himont KS-052P | — | — | 70 |
| Hytrel 4056 | 20 | 20 | 20 |
| Elvaloy HP441 | 5 | 5 | 5 |
| Ampacet 11343 | 5 | 5 | 5 |

TABLE 8

|  | Example 16 | Example 17 |
|---|---|---|
| Himont KS-031P | 65 | 55 |
| Hytrel 4056 | 25 | 35 |
| Elvaloy HP441 | 5 | 5 |
| Ampacet 11343 | 5 | 5 |

TABLE 9

|  | Example 18 | Example 19 | Example 20 | Example 21 |
|---|---|---|---|---|
| Himont KS-063P | 25 | 35 | 49 | 70 |
| Himont KS-031P | 50 | 35 | 21 | — |
| Hytrel 4056 | 15 | 20 | 20 | 20 |
| Elvaloy HP441 | 5 | 5 | 5 | 5 |
| Ampacet 11343 | 5 | 5 | 5 | 5 |

TABLE 10

|  | Example 22 | Example 23 | Example 24 |
|---|---|---|---|
| Himont KT-012P | 25 | 35 | 45 |
| Himont KS-031P | 50 | 35 | 25 |
| Hytrel 4056 | 15 | 20 | 20 |
| Elvaloy HP441 | 5 | 5 | 5 |
| Ampacet 11343 | 5 | 5 | 5 |

TABLE 11

|  | Example 25 | Example 26 | Example 27 | Example 28 |
|---|---|---|---|---|
| Himont KT-012P | 45 | 20 | 45 | 20 |
| Himont KS-031P | 20 | 45 | 10 | 35 |
| Hytrel 4056 | 25 | 25 | 35 | 35 |

TABLE 11-continued

|  | Example 25 | Example 26 | Example 27 | Example 28 |
|---|---|---|---|---|
| Elvaloy HP441 | 5 | 5 | 5 | 5 |
| Ampacet 11343 | 5 | 5 | 5 | 5 |

TABLE 12

|  | Example 29 | Example 30 |
|---|---|---|
| Himont KT-012P | 20 | 25 |
| Himont KS-031P | 45 | 35 |
| Hytrel 4056 | 25 | 35 |
| Elvaloy HP441 | 5 | 5 |
| Ampacet 11343 | 5 | 5 |

EXAMPLES 31 AND 32

A plasticizer, Elvaloy 742, was used in the compositions of Examples 31, 32, 33, 34 and 35. Elvaloy 742 contains ethylene, vinyl acetate and carbon monoxide. The compositions were made in accordance with the procedure set forth in Example 1. The compositions of Examples 31 and 32 are set forth in Table 13. The compositions of Examples 33, 34 and 35 are set forth in Table 14. The polymer blends of Examples 33, 34 and 35 were tumbled-blended in a vee-blender.

The compositions were compounded and pelletized on an American Leistritz ASE-50 twin screw compounding extruder and subsequently extruded into a monofilmanet tube in a David-Standard (1¼ inch single screw) extruder with a spinneret "C"-shaped die. The extruded polymer was quenched, drawn down, annealed and calendered. The resulting polymer monofilments had good physical properties (See Table I).

TABLE 13

|  | Example 31 | Example 32 |
|---|---|---|
| Himont KT-012P | 20 | 20 |
| Himont KS-031P | 35 | 25 |
| Hytrel HTR-6108 | 35 | 45 |
| Elvaloy 742 | 5 | 5 |
| Ampacet 11343 | 5 | 5 |

TABLE 14

|  | Example 33 | Example 34 | Example 35 |
|---|---|---|---|
| Himont KT-012P | 45 | 35 | 20 |
| Himont KS-031P | — | 10 | 25 |
| Hytrel 4056 | 45 | 45 | 45 |
| Elvaloy HP441 | 5 | 5 | 5 |
| Ampacet 11343 | 5 | 5 | 5 |

The floss of Example 33, in its relaxed state, had a thickness of 0.0030 inches. The floss was prepared for use by wrapping the ends around two fingers prior to insertion in the mouth. The floss was subjected to a slight tension and measurement of the thickness taken. The floss, when under slight tension, measured 0.0026 inches in thickness, a reduction of about 13%. In contrast, in most traditional monofilament flosses such as expandable Teflon, the elongation of the monofilament under such tension is about 3–5% without any measurable reduction in thickness.

EXAMPLE 36

Monofilaments were made as described in Example 33, 34 and 35; the composition shown in table 15 contained Pebax 5533 and X1147, both modified polyamides, and Orevac 9314, a compatibilizer (all available commercially from Atochem North America of Philadelphia) and Unitane OR 450, Titanium Dioxide.

TABLE 15

| Pebax 5533 | 80.0 |
|---|---|
| Pebax X1147 | 7.2 |
| Orevac 9314 | 10.8 |
| Unitane OR 450 | 2.0 |

EXAMPLES 37 AND 38

Tables 16 and 17 show compositions made in accordance with the procedure set forth in Examples 33, 34 and 35 containing Pebax 6333, a modified polyamide (available commercially from Atochem North America of Philadelphia) as the base polymer in the compositions of this invention.

TABLE 16

| Pebax 6333 | 80.0 |
|---|---|
| Orevac 9314 | 18.0 |
| Unitane OR 450 | 2.0 |

EXAMPLE 38

TABLE 17

| Pebax 5533 | 80.0 |
|---|---|
| Pebax X1147 | 7.2 |
| Orevac 18211 | 10.8 |
| Unitane OR 450 | 2.0 |

EXAMPLE 39

Table 18 show compositions made in accordance with the procedure set forth in Examples 33, 34 and 35 containing Himont KT-025P, a proprietary terpolymer which is commercially from the Himont Co. of Wilmington, Del., Hytrel 4056, Elvaloy HP441 and pigment.

TABLE 18

| Himont KT-025P | 45.0 |
|---|---|
| Hytrel 4056 | 45.0 |
| Elvaloy HP441 | 5.0 |
| Pigment | 5.0 |

TABLE 1

| EXAMPLE NUMBER | DENIER | THICKNESS (INCH) | WIDTH (INCH) | BREAK STRENGTH | MAXIMUM ELONG | TENACITY % g/D |
|---|---|---|---|---|---|---|
| 1 | 1269 | 0.0039 | 0.0684 | 6.63 | 21.8 | 2.37 |
| 2 | 1129 | 0.0039 | 0.0560 | 6.42 | 18.5 | 2.58 |
| 3 | 1190 | 0.0043 | 0.0555 | 7.00 | 19.4 | 2.67 |
| 4 | 1136 | 0.0047 | 0.0484 | 6.30 | 31.9 | 2.51 |
| 5 | 1143 | 0.0032 | 0.0671 | 6.50 | 32.3 | 2.58 |
| 6 | 1168 | 0.0042 | 0.0521 | 6.08 | 50.7 | 2.36 |

TABLE 1-continued

| EXAMPLE NUMBER | DENIER | THICKNESS (INCH) | WIDTH (INCH) | BREAK STRENGTH | MAXIMUM E-LONG | TENACITY % g/D |
|---|---|---|---|---|---|---|
| 7 | [NO DATA FOR EXAMPLE available] | | | | | |
| 8 | 1382 | 0.0079 | 0.0390 | 7.46 | 46.1 | 2.45 |
| 9 | 1915 | 0.0086 | 0.0518 | 9.87 | 56.0 | 2.34 |
| 10 | 2415 | 0.0086 | 0.0510 | 9.87 | 56.0 | 1.86 |
| 11 | 1439 | 0.0086 | 0.0417 | 8.77 | 60.1 | 2.77 |
| 12 | 1058 | 0.0073 | 0.0358 | 5.83 | 35.5 | 2.50 |
| 13 | 1000 | | | <5.00 | | |
| 14 | 950 | | | <5.00 | | |
| 15 | 900 | | | <5.00 | | |
| 16 | 960 | | | <5.00 | | |
| 17 | 950 | | | <5.50 | | |
| 18 | 960 | | | <5.00 | | |
| 19 | 940 | | | <5.00 | | |
| 20 | 960 | | | <5.00 | | |
| 21 | 940 | | | <5.00 | | |
| 22 | 960 | | | <5.00 | | |
| 23 | 1000 | | | 6.00 | | |
| 24 | 960 | | | 5.80 | | |
| 25 | 950 | | | <5.50 | | |
| 26 | 960 | | | <5.50 | | |
| 27 | 950 | | | 5.50 | | |
| 28 | 960 | | | 5.50 | | |
| 29 | 930 | | | <5.50 | | |
| 30 | 970 | | | 5.50 | | |
| 31 | 960 | | | <5.00 | | |
| 32 | 950 | | | 5.50 | | |
| 33 | 970 | 0.0370 | 0.0450 | 7.13 | 41.7 | 3.34 |
| 34 | 938 | 0.0380 | 0.0500 | 6.15 | 62.1 | 2.98 |
| 35 | 970 | 0.0350 | 0.0510 | 5.11 | 53.6 | 2.39 |

What is claimed is:

1. A process for making a tubular dental hygiene device comprising:
   a) extruding a polymer blend, using an extrusion pump, to form a monofilament tube suitable for processing into said tubular dental hygiene device;
   b) orienting said extruded monofilament tube;
   c) annealing said extruded monofilament tube; and
   d) collapsing said extruded monofilament tube.

2. A process according to claim 1 wherein, during said extrusion step, the extrusion pump is rhythmically pulsed, thereby producing a textured tubing.

3. A process according to claim 1 wherein said polymer blend is extruded into a cooling bath having a temperature of between about 75 and about 80° F.

4. A process according to claim 1 wherein after said extrusion step, said extruded monofilament tube is heated and pulled through Godet rolls.

* * * * *